United States Patent [19]
Patel et al.

[11] Patent Number: 4,855,294
[45] Date of Patent: Aug. 8, 1989

[54] METHOD FOR REDUCING SKIN IRRITATION ASSOCIATED WITH DRUG/PENETRATION ENHANCER COMPOSITIONS

[75] Inventors: Dinesh C. Patel, Murray; Charles D. Ebert, Salt Lake City, both of Utah

[73] Assignee: TheraTech, Inc., Salt Lake City, Utah

[21] Appl. No.: 240,688

[22] Filed: Sep. 6, 1988

[51] Int. Cl.$^4$ .................. A61K 31/55; A61K 31/40; A61K 31/16; A61K 31/10; A61K 31/045
[52] U.S. Cl. .................................. 514/212; 514/424; 514/629; 514/708; 514/724; 514/738; 514/947
[58] Field of Search ............... 514/724, 947, 212, 424, 514/629, 708, 738

[56] References Cited
U.S. PATENT DOCUMENTS 4,537,776  8/1986  Cooper .............................. 514/424
4,695,465  9/1987  Kigasawa et al. .................. 514/947

FOREIGN PATENT DOCUMENTS 43738  1/1982  European Pat. Off. .
95813  12/1983  European Pat. Off. .

OTHER PUBLICATIONS

Remington's Pharmaceutical Sciences, 15th ed., 1975, p. 715.

*Primary Examiner*—Douglas W. Robinson
*Assistant Examiner*—Raymond J. Henley, III
*Attorney, Agent, or Firm*—Thorpe, North & Western

[57] ABSTRACT

A composition and method for reducing the skin irritation properties of a transdermal drug/enhancer composition which comprises incorporating into said composition, either prior to or at the time of application the skin, an effective amount of glycerin. When incorporated into the drug/enhancer composition prior to application to the skin the glycerin content will be between about 0.1 and 70 wt. %, preferably between about 1.0 and 50 wt. % and most preferably between about 5.0 and 20 wt. % of the composition.

21 Claims, No Drawings

METHOD FOR REDUCING SKIN IRRITATION ASSOCIATED WITH DRUG/PENETRATION ENHANCER COMPOSITIONS

FIELD OF THE INVENTION

The invention relates generally to reducing skin irritation in drug/permeation enhancer compositions formulated for transdermal administration. More particularly, the invention relates to the use of glycerin to reduce the skin irritation frequently associated with permeation enhancer mediated transdermal drug delivery. The invention thus encompasses a method of reducing skin irritation by co-administering various transdermal, enhancercontaining compositions with glycerin. The invention also extends to compositions for transdermal administration which are formulated to contain glycerin.

BACKGROUND OF THE INVENTION

The delivery of drugs through skin provides many advantages; primarily, such a means of delivery is a comfortable, convenient and non-invasive way of administering drugs. The variable rates of absorption and metabolism in oral treatment are avoided, and other inherent inconveniences—e.g., gastrointestinal irritation and the like—are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the bloodstream of lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs.

To increase skin permeability, an in particular, to increase the permeability of the stratum corneum (i.e., so as to achieve enhanced penetration, through the skin, of the drug to be transdermally administered), the skin may be treated with one or more permeation enhancing agents (or "permeation enhancers", as sometimes referred to herein) prior to administration of the drug. Alternatively, and preferably, the drug and permeation enhance are simultaneously applied or co-delivered.

Various such compounds for enhancing the permeability of skin are known in the art. U.S. Pat. Nos. 4,006,218, 3,551,554 and 3,472,931, for example, respectively describe the use of dimethylsulfoxide (DMSO), dimethyl formamide (DMF) and N,N-dimethylacetamide (DMA) to enhance the absorption of topically applied drugs through the stratum corneum. Other compounds which have been used to enhance skin permeability include: decylmethylsufloxide ($C_{10}MSO$); polyethylene glycol monolaurate (PEGML; see e.g., U.S. Pat. No. 4,568,343; the 1-substituted azacycloheptan-2-ones, particularly 1-n-dodecyl-cyclazacycloheptan-2-one (available under the trademark "Azone" from Nelson Research & Development Co., Irvine, CA; see U.S. Pat. Nos. 3,989,816, 4,316,893, 4,405,616 and 4,557,934); "cell envelope disordering" compounds such as methyl laurate or oleic acid in combination with solvents such as N-2-hydroxyethyl) pyrrolidone (U.S. Pat. No. 4,537,776) or $C_3$-$C_4$ diols (U.S. Pat. No. 4,552,872, EPA 043738). U.S. Pat. No. 4,593,048 also discloses a composition stated to promote drug adsorption by the skin, the composition containing a major amount of a lower alcohol and lesser amounts of various 6–24C hydrocarbons.

The disadvantage of using many permeation enhancers is that they are often quite irritating to the skin. Attempts to reduce the skin irritation that results from permeation enhancers have not proven very successful. The inventors herein have now provided a solution to the problem, by virtue of having discovered that glycerin is effective as a topical anti-irritant in reducing skin irritation from generally mildly to moderately irritating drug/permeation enhancer combinations. However, the terms "mildly" and "moderately" are relative terms and the invention may function equally well in certain "severely" irritating drug/permeation enhancer combinations.

Glycerin is well known as an emollient, such as taught in U.S. Pat. No. 4,687,481, and is used in the manufacture of cosmetics and soaps. However, applicants are unaware of any teaching in the art to the effect that glycerin is an effective anti-irritant when administered in combination with a wide variety of irritation producing drug/permeation enhancer compositions. In fact, when glycerin is applied to rectal tissues for use as a laxative in children, it is stated to cause dehydration of mucosal tissues to produce an irritant effect. *Physicians Desk Reference*, 41st Edition, Medical Economics Company, Oradel, N.J. 1987, p. 931.

The following references provide a general overview of anti-irritants: J. P. Guillot et al., *Int. Journal of Cosmetic Sci.* 5:255–265 (1983); R. L. Goldemberg, "Antiirritants" in *Principles of Cosmetics for the Dermatologist*, Phillip Frost & Stephen N. Horwitz, eds., London: The C.V. Mosby Company, 1979; R. L. Goldemberg, *J. Soc. Cosmet. Chem.* 30:415–427 (Dec. 1979); and U.S. Pat. No. 4,695,456 to Wilder (summarizes theories relating to the processes involved in chemical irritant injury). The Guillot et al. paper is particularly relevant here, as it teaches that glycerin is ineffective as an anti-irritant (id. at p. 263), contrary to applicants' present discovery.

Summary of the Invention

Accordingly, it is a primary object of the present invention to provide a method for reducing skin irritation associated with all irritating drug/permeation enhancer combinations formulated for transdermal administration for which it is effective, the method comprising applying glycerin to a selected area of skin in combination with the selected drug/permeation enhancer composition.

It is still another object of the invention to provide a composition for transdermal administration of a selected drug, the composition containing glycerin as an anti-irritant in addition to drug and permeation enhancer.

In one aspect of the invention, a method is provided for reducing the skin irritation associated with irritating drug/enhancer compositions, the method comprising applying an effective amount of glycerin to a predetermined area of skin in combination with the selected drug and permeation enhancer. The composition which is applied may include glycerin in combination with carriers, vehicles, or the like. The composition may also contain a mixture of drugs and/or a mixture of permeation enhancers. While the invention has been found to be most effective in reducing skin irritation associated with drug/permeation enhancer formulations producing mild to moderate skin irritations, it is to be recognized that not all subjects react equally to the same formulation. Hence, what may produce mild irritation on the skin of one subject might produce severe irritation on another. Also, the addition of glycerin might reduce severe irritation on one subject more than moderate or mild irritation on another. Therefore, the invention is directed generally to reducing any grade of skin irritation caused by any caused drug/permeation enhancer combination for which it is effective.

DETAILED DESCRIPTION

By cutaneous "irritation" as used herein is meant a wide range of adverse skin reactions resulting from chemical or other irritants. Typically, the adverse skin reactions are primary skin irritation reactions that result in localized inflammation or injury. As noted by Guillot et al., supra, the exact nature of such skin irritation varies with chemical structure and concentration of the irritant, duration of contact with skin, and the rate of penetration of the irritant. The immune system is not involved. The various mechanisms believed to be involved in primary skin irritation are described in Guillot et al., the disclosure of which is incorporated herein by reference.

"Mildly", "moderately" or "severely" irritating compositions, while relative terms, are those having an irritation index as defined under "Experimental", below and particularly in reference to Table X.

"Penetration enhancement" or "permeation enhancement" as used herein relates to an increase in the permeability of skin to a drug, i.e., so as to increase the rate at which the drug permeates through the skin. The enhances permeation effected through the use of such enhancers can be observed, for example, by measuring the rate of diffusion of drug through animal or human skin using a diffusion cell apparatus. The diffusion cell is described by Merritt et al.. Diffusion Apparatus for Skin Penetration, *J. of Controlled Release*, 1 (1984) pp. 161-162.

By "transdermal" delivery, applicants intend to include both transdermal (or "percutaneous") and transmucosal administration, i.e., delivery by actual passage of a drug through the skin or mucosal tissue.

By "afflicted situs" is meant a localized area of pathology, discomfort, infection, inflammation or lesion, and the immediately surrounding area.

By "application situs" is meant a site suitable for topical application with or without the means of a mechanical sustained release device, patch or dressing, e.g., behind the ear, on the arm, back chest, stomach, leg, top of foot, etc.

"Carriers" or "vehicles" as used herein refer to carrier materials suitable for transdermal drug administration, and include any such materials known in the art, i.e., any liquid, gel, solvent, liquid diluent, or the like, which is nontoxic and which does not interact with other components of the composition in a deleterious manner. Carriers are used to provide the compositions of the invention in their preferred liquid form. Examples of suitable carriers for use herein include water, mineral oil, silicone, polyethylene glycol, polypropylene glycol, liquid sugars, waxes, petroleum jelly and a variety of other oils and polymeric materials.

By the term "pharmacologically active agent" or "drug" is meant any chemical material or compound suitable for transdermal or transmucosal administration which induces a desired biological or pharmacological effect by topical application to the "affliction situs" or by systemic delivery from the "application situs" to a desired target area. Such substances include the broad classes of compounds normally delivered through body surfaces and membranes, including skin. In general, this includes therapeutic agents in all of the major therapeutic areas including, but not limited to, anti-infectives such as antibiotics and antiviral agents, analgesics and analgesic combinations, anorexics, anthemidines, antiarthritics, antiasthmatic agents, anticonvulsants, antidepressants, antidiabetic agents, antidiarrheals, antihistamines, antiinflammatory agents, antimigraine preparations, antimotion sickness agents, antinauseants, antineoplastics, antiparkinsonism drugs, antipruritics, antipsychotics, antipyretics, antispasmodics, including gastrointestinal and urinary, anticholinergics, sympathomimetics, xanthine derivatives, cardiovascular preparations including calcium channel blockers, beta-blockers, antiarrhythmics, antihypertensives, diuretics, vasodilators including general coronary, peripheral and cerebral, central nervous system stimulants, cough and cold preparations, decongestants, diagnostics, hormones (both steroidal and non-steroidal), hypnotics, immunosuppressives, muscle relaxants, parasympatholytics, parasympathomimetics, psychostimulants, sedatives and tranquilizers.

By "effective" amount of a drug or pharmacologically active agent is meant a nontoxic but sufficient amount of a compound to provide the desired local or systemic effect and performance at a reasonable benefit/risk ratio attending any medical treatment. An "effective" amount of a permeation enhancer as used herein means an amount selected so as to provide the desired increase in skin permeability and, correspondingly, the desired depth of penetration, rate of administration and amount of drug delivered. By "effective amount" of an anti-irritant is meant a quantity sufficient to noticeably reduce cutaneous irritation as defined above.

In the preferred embodiment of the present invention, glycerin is used to reduce the skin irritation associated with irritating drug/enhancer compositions, typically irritation resulting from use of common permeation enhancers such as ethanol, propylene glycol, dimethyl sulfoxide (DMSO), Azone TM, the cell envelope disordering compositions of U.S. Pat. Nos. 4,537,776 and 4,552,872, cited supra, and the like. The method involves treating the skin with glycerin prior to or concurrently with administration of a drug/enhancer composition. The glycerin may be applied, neat, just prior to the administration of a drug/enhancer composition. Alternatively, in the preferred embodiment, the drug/enhancer composition that is to be transdermally administered is formulated so as to contain an effective amount of glycerin. The composition may, in addition, include one or more selected carriers, vehicles, or excipients, and various agents and ingredients commonly employed in dermatological and cosmetic ointments, lotions or other preparations. For examples, fragrances, opacifiers, preservatives, anti-oxidants, gelling agents, perfumes, thickening agents, stabilizers, surfactants, emollients, coloring agents,and the like may be present.

In the preferred embodiment, i.e., in which a composition for transdermal administration is formulated to contain an effective amount of glycerin, the proportions of various drug and enhancer components are those typically in use. In other words, specific amounts of drug and/or enhancer are not critical and do not form part of the invention. The amount of glycerin making up an "effective amount" is normally in the range of about 0.1 to 70 wt. %, preferably between about 1.0 and 50 wt. % and most preferably in the range of about 5 to 20 wt%. It will be appreciated by those skilled in the art that the relative amounts of the components in these compositions can vary a great deal. For example, the amount of drug present in the composition will depend on a variety of factors, including the disease or condition to be treated, the nature and activity of the drug, the desired effect, possible adverse reactions, the ability and speed of the drug to reach its intended target, the cost and availability of the drug, and other factors within the particular knowledge of the patient and physician. The amount of enhancer present in the composition will similarly depend on a number of factors, e.g., on the depth of cutaneous penetration desired, the strength of the particular enhancer, and the like.

While the invention is directed to the use of glycerin in combination with any enhancer composition there are certain enhancer solvents and cell-envelope disordering compounds which are preferred. Preferred cell-envelope disordering compounds are members selected from the group consisting of methyl laurate, oleic acid, oleyl alcohol, glycerol monooleate, glycerol dioleate and glycerol trioleate and mixtures thereof. Preferred solvents are members selected from the group consisting of a $C_2$ or $C_3$ alcohol, a $C_3$ or $C_4$ diol, DMSO, DMF, DMA, 1-n-dodecyl-cyclazacycloheptan-2-one. N-methyl-pyrrolidone and N-(2-hydroxyethyl)pyrrolidone and mixtures thereof.

The method of delivery of the present compositions may also vary, but necessarily involves applying the selected composition to the skin or other tissue for a period to time sufficient to provide desired pharmacological or biological response. When applied to an "afflicted situs" the method may involve direct application of the composition as an ointment, gel, cream, lotion, or the like. When applied to an "application situs" for systemic delivery to another location the method may involve use of a drug delivery device as taught, for example, in U.S. Pat. Nos. 3,742,951, 3,797,494 or 4,568,343. As noted above, glycerin is preferably co-administered with the drug/enhancer composition, but can also be used to pretreat the skin, i.e., prior to application of the transdermal formulation.

Preferred drug delivery devices include a drug/permeation enhancer reservoir wherein the reservoir contains the drug/enhancer/glycerin combination in liquid form or gelled or thickened by an agent such as mineral oil, petroleum jelly and various aqueous gelling agents and hydrophilic polymers. The reservoir is brought in contact with the skin at the application situs and is held in place on the skin at the application situs and is held in place on the skin using a suitable adhesive as described, for example, in U.S. Pat. No. 4,568,343, supra and the drug/enhancer/glycerin combination is applied to the skin through a membrane forming the reservoir floor which is in contact with the skin. In a preferred embodiment, glycerin is incorporated into the drug/permeation enhancer reservoir; alternatively, as above, glycerin may be used instead to pretreat the skin prior to application of the drug delivery device.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

Experimental

Preparation of Drug/Enhancer Compositions

Compositions for respective drug/enhancers are listed in Tables 1-8. The polar phases (i.e. water, ethanol, glycerin, DMSO, propylene glycol as listed in respective tables) were first mixed together with a sufficient quantity of Carbopol 1342 to provide a 1.0% (w/v) Carbopol content. Respective drugs were then added to the mixtures at levels to provide saturation at 32° F.(0° C.) in final composition. The mixtures were homogenized with a Virtus tissue homogenizer at 1000 rpm for 2 minutes. The non-polar phases (methyl laurate, glycerol monooleate, glycerol dioleate, oleic acid, etc.) were then added to the mixtures, when necessary, and emulsified for one minute at 1000 rpm. Resultant drug/enhancer compositions were used as is in skin flux and primary skin irritation studies.

Skin Flux Studies

The in vitro human cadaver skin rates were measured using non-jacketed permeation cells. The temperature of the cells was maintained at 32° C. by placing the cells in an aluminum heating block that is positions in a stirring-heating module (Pierce Chemical Company, Rockford, Illinois). The epidermis was separated from the human cadaver whole skin by the heat-separation method of Kligman and Christophers (*Arch. Dermatol.* 88:702 (1963)) involving exposure of the full thickness skin to 60° C. heat for 60 seconds, after which time the epidermis was gently peeled off from the dermis. The epidermis was placed between the two halves of the permeation cell with stratum corneum layer facing the donor compartment. Test formulations were placed on the stratum corneum. Phosphate buffered saline (PBS) containing 0.02% sodium azide was placed in the receiver compartment in contact with the dermal side of the epidermis. Samples were then withdrawn from the receiver compartment at predetermined times and analyzed by HPLC.

The drug flux ($mg/cm^2/hr$) across human skin was calculated from linear regression analysis of the cumulative amount of drug permeated across skin ($mg/cm^2$) versus time (hours).

Primary Skin Irritation

Primary skin irritation was evaluated for each formulation in 6 albino rabbits. The back of each animal was shaved 24 hours prior to test sample application. The gelled test samples were applied to the backs of the animals using 1 $cm^2$ Finn TM Chambers containing 0.1 cc of test sample. The entire abdomen of the animals was then wrapped with surgical tape to prevent the animals from removing the Finn chambers. After 24 hours of exposure, the Finn Chambers were removed from the animals backs. Any residual test sample adhering to the animals' skin was gently removed with surgical gauze and distilled water. Test sites were scored for erythema and edema at 1 hour and 48 hours following removal of the test sample using the scoring scale described in Table X. The irritation index (II) was then calculated for each test sample as sum of all edema and erythema scores in all test animals divided by the number of animals evaluated (n=6) and the number of parameters scored (edema+erythema=2).

EXAMPLE 1

Estradiol compositions were formulated using ethanol and water as an enhancer system with all but the base formulation containing glycerin in varying amounts as indicated in Table I. Flux and irritation indices were evaluated as described above, and results are set forth in Table I. All compositions were found to be substantially non-irritating. It is significant to note that glycerin had no effect of the flux at glycerin concentrations ranging from 10 to 40% thereby demonstrating that glycerin does not function as an enhancer. It is also significant to note that the flux of commercially formulated Estraderm was considerably less than the flux of estradiol formulated with an enhancer system yet there was some irritation noted with Estraderm.

TABLE I

| Drug | Enhancer Composition (% v/v) | | | Flux $\mu g/cm^2/hr$ | Irritation Index |
|---|---|---|---|---|---|
| | EtOH | H$_2$O | Glycerin | | |
| Estradiol | 60 | 40 | — | 0.86 | 0 |
| Estradiol | 60 | 30 | 10 | 0.93 | 0 |
| Estradiol | 60 | 20 | 20 | 0.84 | 0 |
| Estradiol | 60 | — | 40 | 0.91 | 0 |
| Estraderm TM (control) | | | | 0.35 | 0.5 |

Estraderm is a tradename of Ciba-Giegy for an estradiol transdermal system consisting of a patch housing a gelled alcohol reservoir containing the estradiol which is transmitted through a rate limiting membrane in the patch onto the skin to provide nominal in vivo delivery of 50 micrograms of estradiol per day through the skin.

EXAMPLE 2

The effect of glycerin on calcitriol flux and skin irritation resulting from binary enhancers consisting of ethanol and methyl laurate was evaluated. The results are set forth in Table II.

Ethanol/water (75/25) produced minimal irritation, but no skin flux (all experiments were conducted using 100 micrograms/ml calcitriol concentration in all enhancers). Incorporation of methyl laurate (as a cell-envelope disordering agent/lipid fluidizer) significantly increased calcitriol flux (0.55 $\mu g/cm^2/hr$ vs. 0) and also increased irritation (index of 3.5 vs. 0.1). Incorporation of glycerin (7.5%) reduced the irritation index (II) from 3.5 to 2.3, a 34% reduction, while not affecting flux. Lowering the ethanol concentration from 75% to 67.5% further reduced irritation to and index of 1.6 while not reducing flux. These results demonstrate that glycerin significantly reduces irritation of moderately irritating percutaneous drug enhancer compositions, while not decreasing skin flux.

TABLE II

| Drug | Enhancer Composition (% v/v) | | | | Flux $\mu g/cm^2/h$ | Irritation Index |
|---|---|---|---|---|---|---|
| | EtOH | H$_2$O | Glycerin | Methyl Laurate | | |
| Calcitriol | 75 | 25 | — | — | 0 | 0.1 |
| Calcitriol | 75 | 21.25 | — | 3.75 | 0.55 | 3.5 |
| Calcitriol | 75 | 13.75 | 7.5 | 3.75 | 0.50 | 2.3 |
| Calcitriol | 67.5 | 21.75 | 7.5 | 3.25 | 0.55 | 1.5 |

EXAMPLE 3

Estradiol composition containing 40:10 ethanol:glycerol dioleate as a binary enhancer and varying amounts of glycerin were evaluated with respect to skin flux and irritation. The results are set forth in Table III. Ethanol along (40% in H$_2$O) produced minimal irritation (II of 0.1) and a flux of 0.39 $\mu g/cm^2/hr$. Incorporation of the cell-envelope disorganizer, glycerol dioleate (GDO), approximately doubled the flux (0.74 $\mu g/cm^2/hr$), but also increased irritation (II of 0.6). Incorporation of glycerin reduced irritation approximately 50% (II of ~0.3). The effect of glycerin on irritation was found to be approximately constant over a wide range of glycerin concentrations (5 to 30%). Glycerin did not affect flux at any concentration either by increasing or reducing it. These data demonstrate that glycerin can reduce the irritation response of mildly irritating percutaneous drug/enhancer compositions while not affecting skin flux.

TABLE III

| Drug | Enhancer Composition (% v/v) | | | | Flux $\mu g/cm^2/hr$ | Irritation Index |
|---|---|---|---|---|---|---|
| | EtOH | H$_2$O | Glycerin | GDO* | | |
| Estradiol | 40 | 60 | — | — | 0.39 | 0.1 |
| Estradiol | 40 | 50 | — | 10 | 0.74 | 0.6 |
| Estradiol | 40 | 45 | 5 | 10 | 0.66 | 0.3 |
| Estradiol | 40 | 40 | 10 | 10 | 0.69 | 0.4 |
| Estradiol | 40 | 30 | 20 | 10 | 0.68 | 0.3 |
| Estradiol | 40 | 20 | 30 | 10 | 0.71 | 0.3 |
| Estraderm TM (Control) | | | | | 0.28 | 0.7 |

*Glycerol Dioleate

EXAMPLE 4

The procedure of Example 3 was repeated using glycerol monooleate (GMO) instead of the dioleate (GDO). Results are set forth in Table IV. At comparable levels, GMO was significantly more irritating than GDO and produced a moderately irritating response having an index of 1.9. Incorporation of 10% glycerin, and reducing the GMO content accordingly, significantly reduced irritation by about 58% to an index of 0.8 while not affecting skin flux (0.43 and 0.40 $\mu g/cm^2/hr$ with and without glycerin). These data demonstrate that glycerin can reduce the irritation response of moderately irritating percutaneous drug/enhancer compositions, while not affecting skin flux.

TABLE IV

| Drug | Enhancer Composition (% v/v) | | | | Flux μg/cm²/hr | Irritation Index |
|---|---|---|---|---|---|---|
| | EtOH | H₂O | Glycerin | GMO* | | |
| Estradiol | 40 | 40 | — | 20 | 0.40 | 1.9 |
| Estradiol | 40 | 40 | 10 | 10 | 0.43 | 0.8 |

*Glycerol monooleate

EXAMPLE 5

The procedure of Example 3 was repeated using a binary enhancer consisting of 70% propylene glycol and 5% oleic acid. Results are set forth in Table V. Propylene glycol/oleic acid along produced a moderate irritation index response of 1.4. Incorporation of glycerin in the place of water (propylene glycol/oleic acid levels remaining constant), significantly reduced the irritation index from 1.4 to 0.1, i.e. a 93% decrease, while not affecting skin flux (1.52 and 1.61 μg/cm²/hr with and without glycerin). These results demonstrate that glycerin can reduce the irritation response of moderately irritating percutaneous drug/enhancer compositions, while not affecting skin flux.

TABLE V

| Drug | Enhancer Composition (% v/v) | | | | Flux μg/cm²/hr | Irritation Index |
|---|---|---|---|---|---|---|
| | H₂O | Glycerin | Propylene Glycol | Oleic Acid | | |
| Estradiol | 25 | — | 70 | 5 | 1.61 | 1.4 |
| Estradiol | — | 25 | 70 | 5 | 1.52 | 0.1 |

EXAMPLE 6

Pindolol compositions were formulated using DMSO and water as indicated in Table VI. The flux and irritation indices were measured according to the aforementioned procedures. Incorporation of 10% glycerin into the DMSO/water formulation, and reducing the water content accordingly, reduced skin the irritation index from 0.5 to 0.3 with corresponding skin flux values of 0.5 and 0.7 μg/cm²/hr. Consistent with previous examples, these results confirm that glycerin can reduce the skin irritation response of mildly irritating transdermal drug/enhancer compositions, while, again, not adversely affecting the skin flux.

TABLE VI

| Drug | Enhancer Composition (% v/v) | | | Flux μg/cm²/hr | Irritation Index |
|---|---|---|---|---|---|
| | DMSO | H₂O | Glycerin | | |
| Pindolol | 70 | 30 | — | 0.5 | 0.5 |
| Pindolol | 70 | 20 | 10 | 0.7 | 0.3 |

EXAMPLE 7

The effect of glycerin on pindolol skin flux and irritation was evaluated using binary enhancer consisting of 80% propylene glycol and 20% oleyl alcohol. The 80/20 propylene glycol/oleyl alcohol formulation produced a high pindolol flux (~25 μg/cm²/hr) and had a high irritation index response (6.7). Incorporation of 10% glycerin, and reducing the oleyl alcohol content accordingly, had no significant effect on irritation indices (6.3 v. 6.7) or flux (26.6 v 25.0 μg/cm²/hr), demonstrating that glycerin may not affect all drug/enhancer formulations, particularly when the irritation index is in the severe range.

TABLE VII

| Drug | Enhancer Composition (% v/v) | | | Flux μg/cm²/hr | Irritation Index |
|---|---|---|---|---|---|
| | Propylene Glycol | Oleyl Alcohol | Glycerin | | |
| Pindolol | 80 | 20 | — | 25.0 | 6.7 |
| Pindolol | 80 | 10 | 10 | 26.6 | 6.3 |

EXAMPLE 8

The effect of humectants on estradiol skin flux and irritation was evaluated as follows. Glycerin is a well known humectant. To evaluate whether the anti-irritant effect of glycerin is due only to increased hydration of the skin, a series of humectants were evaluated using a binary enhancer consisting of 40% ethanol and 10% GDO. Results are set forth in Table VIII. Estradiol flux without humectant was determined to be 0.48 μg/cm²/hr and the irritation index was 0.6. Incorporation of 20% glycerin reduced the irritation index by 50% to 0.3 and had no effect on flux. Two other humectants, propylene glycol and urea, were also evaluated at the same concentration as glycerin. Propylene glycol (20%) increased flux to 0.79 μg/cm²/hr and increased the irritation index to 0.8. Urea (20% wt/v) reduced flux to 0.21 μg/cm²/hr and increased the irritation index to 1.3. These results demonstrate that the anti-irritation effect of glycerin is a function of more than its humectant properties.

TABLE VIII

| Drug | Enhancer Composition (% v/v) | Flux μg/cm²/hr | Irritation Index |
|---|---|---|---|
| Estradiol | 40/50/10 EtOH/H₂O/GDO* | 0.48 | 0.6 |
| Estradiol | 40/30/20/10 EtOH/H₂O/Glycerin/GDO* | 0.42 | 0.3 |
| Estradiol | 40/30/20/10 EtOH/H₂O/Propylene Glycol/GDO* | 0.79 | 0.8 |
| Estradiol | 40/30/20/10 EtOH/H₂O/Urea/GDO* | 0.21 | 1.3 |
| Estraderm ™ (Control) | | 0.18 | 0.7 |

*Glycerol Dioleate

EXAMPLE 9

The effect of glycerin on irritation resulting from the use of a drug/enhancer combination using 1-n-dodecyl-cyclazacycloheptan-2-one (Azone) was evaluated as indicated in Table IX. As may be concluded from that table, the irritation index of a 55/20/20/5 mixture of ethanol/H₂O/propylene glycol/Azone composition was reduced from 2.3 to 1.5, i.e. by about 35%, by the substitution of glycerin for water. Flux of the model drug compound, estradiol, was not affected significantly.

TABLE IX

| Drug | Enhancer Composition (% v/v) | Flux μg/cm²/hr | Irritation Index |
|---|---|---|---|
| Estradiol | 55/20/20/5 EtOH/H₂O/Propylene Glycol/Azone | 1.75 | 2.30 |
| Estradiol | 55/20/20/5 EtOH/Glycerine/Propylene Glycol/Azone | 1.86 | 1.50 |

TABLE X

Evaluation of Skin Reactions

| | Value |
|---|---|
| Erythema and eschar formation: | |
| No erythema | 0 |
| Very mild erythema (barely perceptible) | 1 |
| Mild but well-defined erythema | 2 |
| Moderate to severe erythema | 3 |
| Severe erythema (beet redness to slight eschar formation (injuries in depth) | 4 |
| Edema formation: | |
| No edema | 0 |
| Very mild edema (barely perceptible) | 1 |
| Mild edema (edges of area well defined by definite raising) | 2 |
| Moderate edema (raised approximately 1 millimeter) | 3 |
| Severe edema (raised more than 1 millimeter and extending beyond the area of exposure) | 4 |

The above examples are representative of the many active drugs or therapeutic agents that can be utilized in the present invention. A listing of a compendium of drugs would serve no useful purpose as the effectiveness of some may have to be determined empirically. Also, the enhancer combinations which have been shown are but illustrative of the many combinations which are within the scope of the invention. The application of the present invention to some enhancers may also have to be empirically determined. In summary, the invention is directed to any drug/enhancer combination wherein the addition of glycerin results in a reduction of the skin irritation index. By following the teachings and guidelines contained herein one skilled in the art will be able to readily determine which formulations glycerin may be incorporated into and effectively utilized in reducing skin irritation without significantly affecting flux of the active ingredient across the stratum corneum.

We claim:

1. A drug-enhancer composition for transdermally administering a drug having reduced skin irritation properties consisting essentially of (a) a percutaneously absorbable drug, (b) a mild to moderately irritating enhancer composition consisting of a solvent selected from the group consisting of a $C_2$ or $C_3$ alcohol, a $C_3$ or $C_4$ diol, DMSO, DMF, DMA, 1-n-dodecyl-cyclazacycloheptan-2-one, N-methyl-pyrrolidone and N-(2-hydroxyethyl)pyrrolidone and mixtures thereof and an effective enhancing amount of a cell envelope disordering compound and (c) an effective amount of glycerin to reduce the irritation of said drug-enhancer composition.

2. The composition of claim 1 wherein glycerin is present in an amount of between about 0.1 and 70.0 wt. %.

3. The composition of claim 1 wherein glycerin is present in an amount of between about 1.0 and 50.0 wt. %.

4. The composition of claim 1 wherein glycerin is present in an amount of between abut 5.0 and 20.0 wt. %.

5. The composition of claim 2 wherein the cellenvelope disordering compounds is a member selected from the group consisting of methyl laurate, oleic acid, oleyl alcohol, glycerol monooleate, glycerol dioleate and glycerol trioleate and mixtures thereof.

6. The composition according to claim 5 wherein the enhancer composition contains ethanol.

7. The composition according to claim 5 wherein the enhancer composition contains DMSO.

8. The composition according to claim 6 wherein the enhancer composition contains methyl laurate.

9. The composition according to claim 6 wherein the enhancer composition contains glycerol dioleate.

10. The composition according to claim 6 wherein the enhancer composition contains glycerol monooleate.

11. The composition according to claim 6 wherein the enhancer composition contains propylene glycol.

12. The composition according to claim 11 wherein the enhancer composition contains 1-dodecyl-azacycloheptan-2-one.

13. The composition according to claim 5 wherein the enhancer composition contains propylene glycol.

14. The composition according to claim 13 wherein the enhancer composition contains oleic acid.

15. A method for reducing skin irritation caused by drug-enhancer compositions having skin irritation properties comprising applying to a predetermined area of skin an effective amount of a drug/enhancer composition consisting essentially of a percutaneously absorbable drug, (b) a mild to moderately irritating enhancer composition consisting of a solvent selected from the group consisting of a $C_2$ or $C_3$ alcohol, a $C_3$ or $C_4$ diol, DMSO, DMF, DMA, 1-n-dodecyl-cyclazacycloheptan-2-one, N-methyl-pyrrolidone and N-(2-hydroxyethyl)pyrrolidone and mixtures thereof and an effective enhancing amount of a cell envelope disordering compound and (c) an effective amount of glycerin to reduce the irritation of said drug-enhancer composition.

16. The method of claim 15, wherein the drug-enhancer composition contains between about 0.1 and 70 wt. % glycerin.

17. The method of claim 15, wherein the drug-enhancer composition contains between about 1.0 and 50 wt. % glycerin.

18. The method of claim 15, wherein the drug-enhancer composition contains between about 5.0 and 20.0 wt. % glycerin.

19. The method of claim 17 wherein the cell envelope disordering compound is a member selected from the group consisting of methyl laurate, oleic acid, oleyl alcohol, glycerol monooleate, glycerol dioleate and glycerol trioleate and mixtures thereof.

20. The method of claim 19 wherein the glycerin containing drug-enhancer composition is administered to an afflicted situs.

21. The method of claim 19 wherein the glycerin containing drug-enhancer composition is administered to an application situs.

* * * * *